(12) United States Patent
Habermehl et al.

(10) Patent No.: US 9,476,859 B2
(45) Date of Patent: Oct. 25, 2016

(54) AUTOMATIC CALIBRATION FOR PHASED ARRAY INSPECTION OF GIRTH WELD

(71) Applicants: Jason Habermehl, Quebec (CA); Benoit LePage, L'Ancienne-Lorette (CA); Guillaume Painchaud-April, L'Ancienne-Lorette (CA)

(72) Inventors: Jason Habermehl, Quebec (CA); Benoit LePage, L'Ancienne-Lorette (CA); Guillaume Painchaud-April, L'Ancienne-Lorette (CA)

(73) Assignee: OLYMPUS NDT, INC., Waltham, MA (US)

( * ) Notice: Subject to any disclaimer, the term of this patent is extended or adjusted under 35 U.S.C. 154(b) by 333 days.

(21) Appl. No.: 14/107,217

(22) Filed: Dec. 16, 2013

(65) Prior Publication Data

US 2015/0168355 A1    Jun. 18, 2015

(51) Int. Cl.
*G01N 29/30* (2006.01)
*G01N 29/04* (2006.01)
*G01N 29/26* (2006.01)

(52) U.S. Cl.
CPC ............ *G01N 29/30* (2013.01); *G01N 29/043* (2013.01); *G01N 29/262* (2013.01); *G01N 2291/2675* (2013.01)

(58) Field of Classification Search
CPC ............ G01N 29/262; G01N 2291/106; G01N 29/30; G01N 2291/2675; G01N 29/043; G01N 29/069; G01N 29/4463; G01N 2291/0289; G01N 2291/044; G01N 2291/2626; G01N 2291/267; G01N 29/4427; A61B 8/4488; A61B 8/4494; A61B 8/587
See application file for complete search history.

(56) References Cited

U.S. PATENT DOCUMENTS

| | | | |
|---|---|---|---|
| 9,282,945 B2* | 3/2016 | Smith | A61B 8/00 |
| 2013/0247350 A1* | 9/2013 | Specht | A61B 8/00 29/407.09 |
| 2014/0043933 A1* | 2/2014 | Belevich | A61B 8/587 367/11 |
| 2014/0058266 A1* | 2/2014 | Call | A61B 8/14 600/448 |
| 2014/0219059 A1* | 8/2014 | Younghouse | G01N 29/262 367/87 |
| 2014/0238136 A1* | 8/2014 | Ten Grotenhuis | G01N 29/0654 73/592 |

* cited by examiner

*Primary Examiner* — Daniel S Larkin
*Assistant Examiner* — Jamar Ray
(74) *Attorney, Agent, or Firm* — Ostrolenk Faber LLP (57) ABSTRACT

A calibration method for calibrating a phased array probe that is used for testing girth welds for defects. The method utilizes a calibration device on which is defined a series of reflectors that correspond to a series of target zones. The phased array probe is placed via a wedge relative to the calibration device and the phased array probe is configured with an initial set of acoustic parameters which define at least a transmitting aperture, a receiving aperture and a beam steering angle. Using a Full Matrix Capture (FMC) acquisition process and a ray-tracing module, the values of the initial set of acoustic parameters are optimized to evolve a final set of acoustic parameters which the phased array probe utilizes for testing actual devices for weld defects.

15 Claims, 6 Drawing Sheets

AUTOMATIC CALIBRATION FOR PHASED ARRAY INSPECTION OF GIRTH WELD

FIELD OF THE INVENTION

This invention relates to non-destructive testing and inspection systems (NDT/NDI) and more particularly to automation of calibration for a girth weld pipe inspection system using phased array ultrasound technology (PAUT). The invention also relates the use of Full Matrix Capture (FMC) acquisition schemes to predict PAUT parameters through an automated calibration process according to the present disclosure.

BACKGROUND OF THE INVENTION

The use of PAUT for the inspection of pipeline girth weld has been described in various publications such as "Pipeline Girth Weld Inspection using Ultrasonic Phased Arrays" (by Michael Moles, Noel Dube, Simon Labbé, Ed Ginzel). The practice is also incorporated in industrial standard practice such as ASTM E-1961-11 "Standard Practice for Mechanized Ultrasonic Testing of Girth Welds Using Zonal Discrimination with Focused Search Units".

Practically, this inspection is based on the zone discrimination technique which involves the definition of and calibration of multiple beams to obtain desired detection performance on a set of pre-defined artificial defects. The PAUT beams use a pitch-catch configuration which means each beam is impacted by the definition of a transmitter and a receiver. The calibration itself is then relatively complex and time consuming because of the large number of possible settings for each beam.

Furthermore, since the required configuration is dependent on the specific weld geometry to be inspected, a new calibration is required every time changes are made to the inspection system. For calibration of pitch-catch inspection with the zone discrimination technique, an inspector needs to calibrate for each zone of interest in a calibration block to be sure to meet inspection criteria for all potential defects. More specifically, for each zone, the inspector needs to align the probe on the relevant calibration reflector, to adjust the steering angle, the aperture (position and size) and focalization of the transmitter, the aperture of the receiver (position and size), focalization and the gain of the receiver to perform calibration. With today's methods, due to the plurality of calibration reflectors, a typical calibration procedure takes several hours to perform and requires a high degree of expertise by the operator.

A side effect of the current level of complexity of the calibration is a compromise in calibration requirement between realistic calibration time and performance.

PAUT Girth weld inspection is the most common example of the use of pitch-catch PAUT, but it must be understood that the same or similar limitations are found in most systems that rely on pitch-catch PAUT.

So, there is therefore a need for a method to automate the calibration process of pitch-catch PAUT inspection in order to reduce the calibration time and the dependency on inspector's skills.

There's also a need for a method that would meet tighter calibration tolerance than current PAUT inspection methods in order to improve detection performances and reproducibility.

SUMMARY OF THE INVENTION

This invention uses FMC acquisition technique to find the best acoustic configuration of PAUT beam to reach calibration requirements within each zone to be covered by the inspection; each zone being associated to an artificial reflector on a known reference sample. The FMC acquisition technique is known to include all physical information required to build a PAUT signal in post processing. Therefore a single FMC acquisition can be used to evaluate the inspection result that would have been obtained using any PAUT inspection.

An optimization method is disclosed to define the set of acoustic parameters required for generating and receiving the PAUT beams that would provide the best performances for each target reflector based on the set of FMC data. This method uses operator inputs such as probe position and inspected component definition to define theoretical beam configurations. From this theoretical configuration and including tolerances representative of the application for each parameter involved, the optimization process automatically defines the best calibration values to reach the application requirements.

DETAILED DESCRIPTION OF PREFERRED EMBODIMENTS

Figure 1:
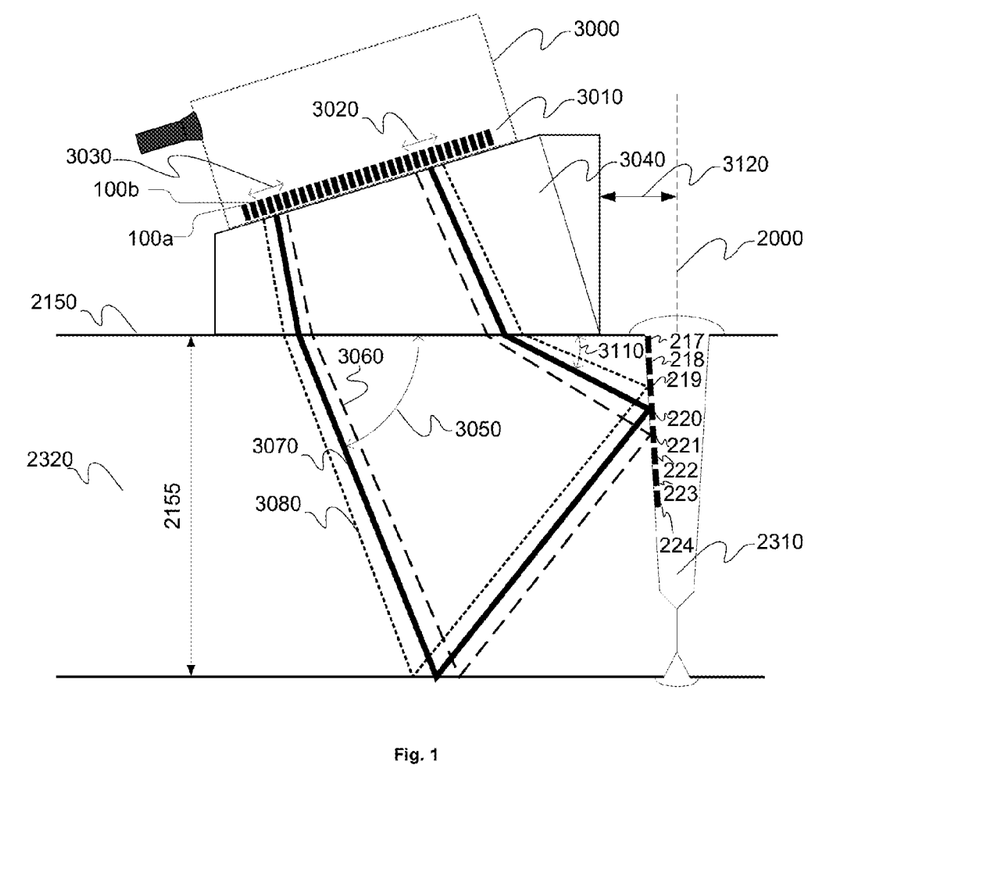
FIG. 1 is a side view representation of the pitch-catch PAUT inspection configuration associated with girth weld inspection.

FIG. 1 shows a phased array probe (PAP) 3000, of the type used for phased array ultrasound testing (PAUT). A side view representative of a PAUT pitch-catch inspection configuration for detecting a set of planar flaws in a girth weld is illustrated on FIG. 1. The ray-tracing representation of the PAUT beam 3070 is a simplified illustration of the acoustic energy path associated to the generation of an acoustic wave by a first aperture 3030 with a first set of delays and received by the second aperture 3020 with a second set of delays. Generation and reception apertures are defined by the position and number of PAUT element 100 included in the so called aperture. As for the delays, they are typically being used to change steering angle 3050 for the acoustic wave generation, the steering angle 3110 for the acoustic wave reception of the beam and the focalization distance of the acoustic wave.

Also represented on the FIG. 1 is a set of reflectors 217, 218, 219, 220, 221, 222, 223 and 224. Those reflectors will be referred to as the TARGET in this document; they represent a set of artificial reflectors machined on the calibration block 2320. A number of beams corresponding to the number of targets are generated, each beam being associated to a specific TARGET. For example, on FIG. 1, beam 3060 is associated to TARGET 219, beam 3070 is associated to TARGET 220, and beam 3080 is associated to TARGET 221. Eventually, the objective of the calibration is to define the set of acoustic parameters (aperture width and position, steering angle and focalization for transmitter and receiver) required for each of the beams to obtain an optimized detection of the each associated TARGET for a real inspection configuration.

Figure 2:
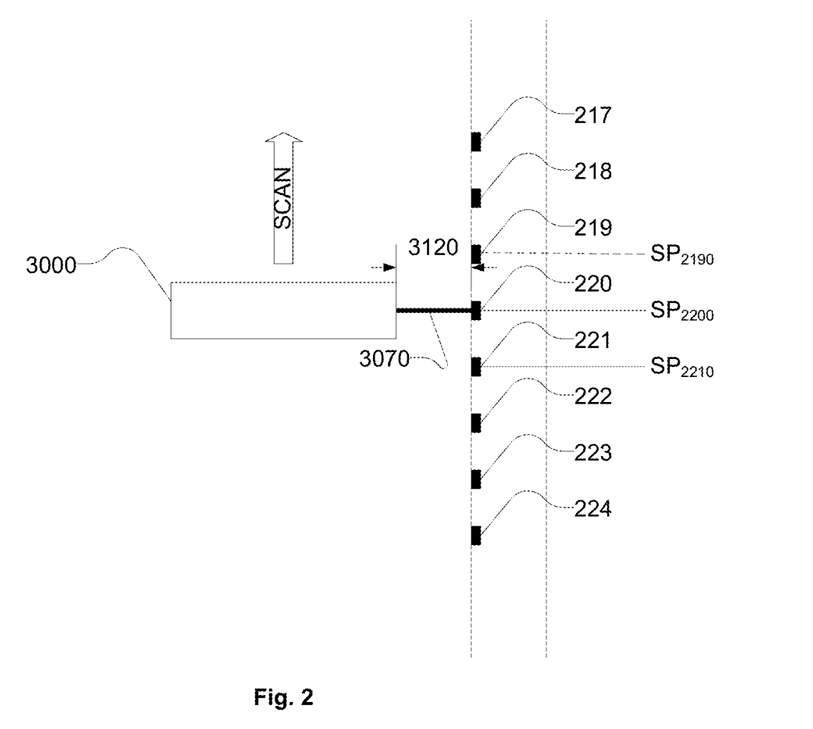
FIG. 2 is a top view representation of the pitch-catch PAUT inspection configuration associated with girth weld inspection.
Figure 3A:
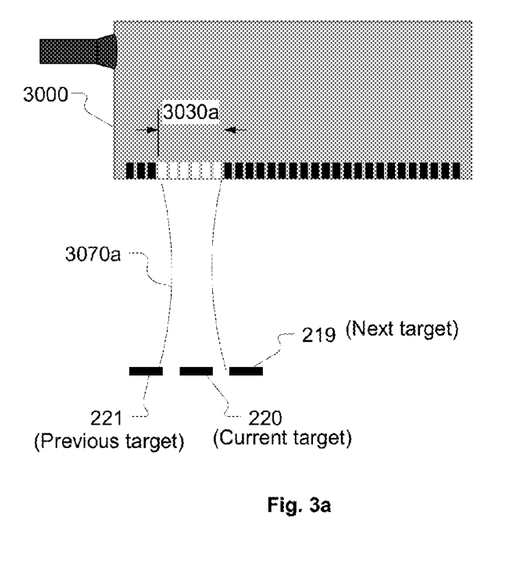
FIGS. 3a and 3b are the representation of a first PAUT aperture, the associated response on a given set of reference flaws and illustrating how the aperture affects the detection of previous and next target.
Figure 3B:
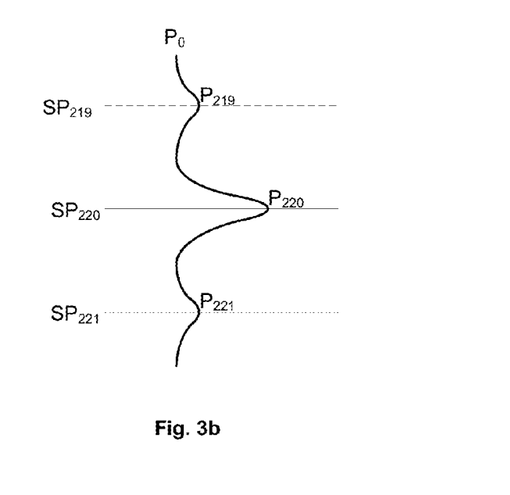
Figure 4A:
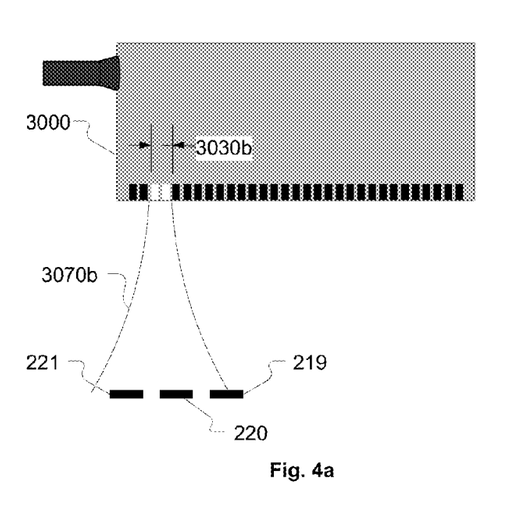
FIGS. 4a and 4b are the representation of a second PAUT aperture, the associated response on a given set of reference flaws and illustrating how the aperture affects the detection of previous and next target.
Figure 4B:
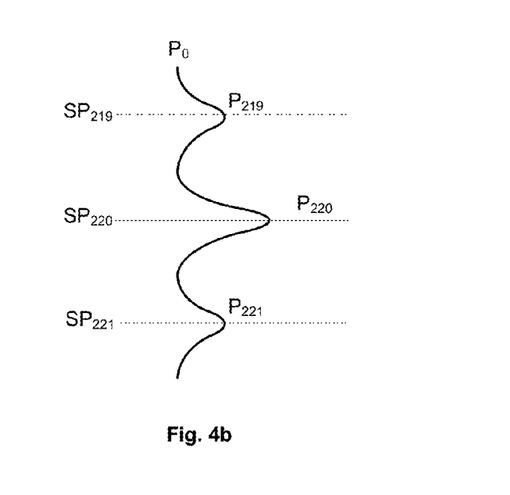

As illustrated on FIG. 2, which is a top view representation of the inspection, the various TARGET are positioned at different scan position (SP) on the calibration bloc in order to decouple the detection of each TARGET relative to the beams. The SP of each TARGET on the block is a known parameter for the inspection although this knowledge is only accurate to within certain tolerance. In this document, the various TARGET are sequentially distributed in the calibration block (i.e. the previous an next TARGET to 220 relative to the scan position on FIG. 2 are also the previous and next TARGET to 220 on the side view of FIG. 1), this representation is only to simplify the discussion and is not a limitation of the method. Reference made to previous and next TARGET for the method of the invention must be understood from the side view representation of FIG. 1.

Another aspect to consider for the calibration is the detection level obtained by a given beam 3070 on previous 221 and next 219 TARGET. Typically, the objective is to have about 10 dB less amplitude on previous and next TARGET relative to the current TARGET, tolerances over and above this value are then provided for defining the calibration success. Aperture width and focalization are the key acoustic parameters for reaching this objective. The FIGS. 3a, 3b and FIGS. 4a and 4b are simplified representation of the effect of varying transmitter aperture width 3030a to 3030b on the signal amplitude at $SP_{219}$, $SP_{220}$ and $SP_{221}$. With the larger aperture 3030a, the peak amplitudes $P_{219}$ and $P_{221}$ obtained at $SP_{219}$ and $SP_{221}$ are approximately 12 dB below the peak amplitude $P_{220}$ of the TARGET defect at $SP_{220}$. With the narrow aperture 3030b, the peak amplitudes $P_{219}$ and $P_{221}$ obtained at $SP_{219}$ and $SP_{221}$ are approximately 6 dB below the peak amplitude $P_{220}$ of the TARGET defect at $SP_{220}$. Similar effect would be obtained by varying the receiver aperture 3020. As for the focalization, it must be understood that difference between the current and next/previous TARGET will be maximum when the transmitter and receiver focalization is precisely on the TARGET. So, focalization is another parameter to consider for precisely achieving a 10 dB between current and next/previous TARGET.

Figure 5:
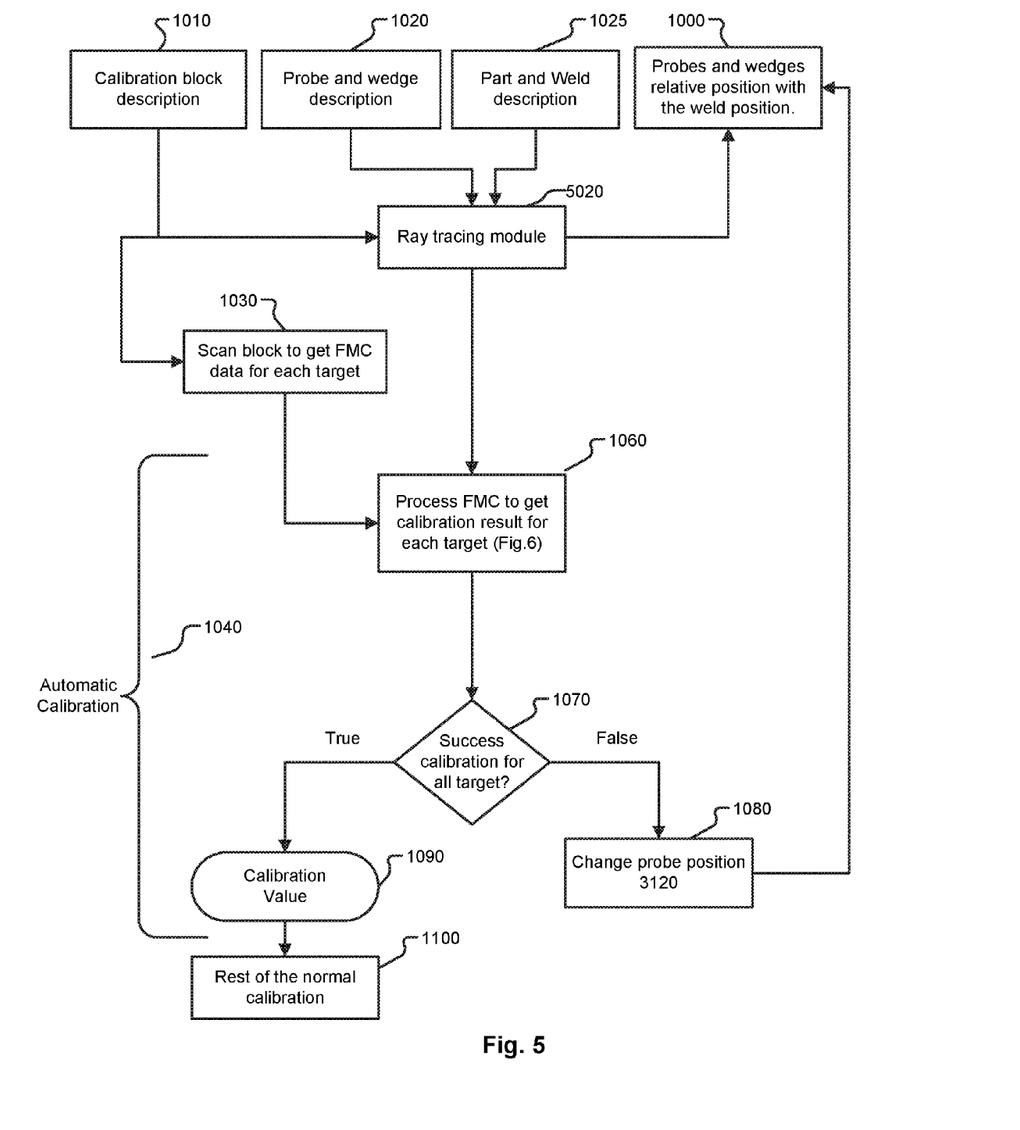
FIG. 5 is a general flow chart exhibiting the automatic calibration process according to the present disclosure for a girth inspection using PAUT and FMC scheme.

Now looking at FIG. 5 which provides a global view of the calibration process including the automated aspects covered by the invention, it is observed that the two sources of inputs for the automatic calibration 1040 are the ray-tracing module 5020 and the set of full matrix capture (FMC) data 1030 acquired on each TARGET. The FMC data is acquired at a relevant scan position for each TARGET (i.e. including known mechanical tolerances). Technically, if those FMC data includes all elements 100 of the transmitter and receiver aperture for a given TARGET, any phase array (PAUT) beam can be precisely simulated from those data in order to conduct the automated calibration process 1060 for this TARGET.

The ray tracing module 5020 uses known information 1020 on the probe 3010 and wedge 3040 assembly 3000. That information typically includes the size and pitch of the probe element 100 as well as the precise localization of these elements relative to the part upper surface 2150. The ray tracing module 5020 also uses information pertaining to the part description 1025 as well as the calibration bloc description for zonal break-down. That information typically includes the inspected part thickness 2155 and the details of the weld 2310 geometry. Another information required by the ray-tracing module 5020 is the position 3120 of the probe assembly 3000 relative to the weld centerline 2000. The ray-tracing module is then able to theoretically predict all beam configurations required for detecting each and every TARGET. The calibration process 1060 will then use this theoretical information to restrain the calibration in relation to known practical tolerances.

Still looking at FIG. 5, we illustrate the fact that the calibration 1060 must successfully achieve the calibration on all TARGET (step 1070) in order to complete the process and provide a set of calibration values in 1090 allowing the remainder of the normal calibration process 1100 to be conducted (including GAIN setting and a validation scan with PAUT). Typically, the calibration will not be met for all targets if the probe is too close or too far from the weld. In this case, the required aperture position and length can't be achieved with the actual probe position 3120 and it may be possible to indicate to the user how (in which direction) to move the probe from the previous failed calibration 1060 in order to make a new calibration scan.

Figure 6:
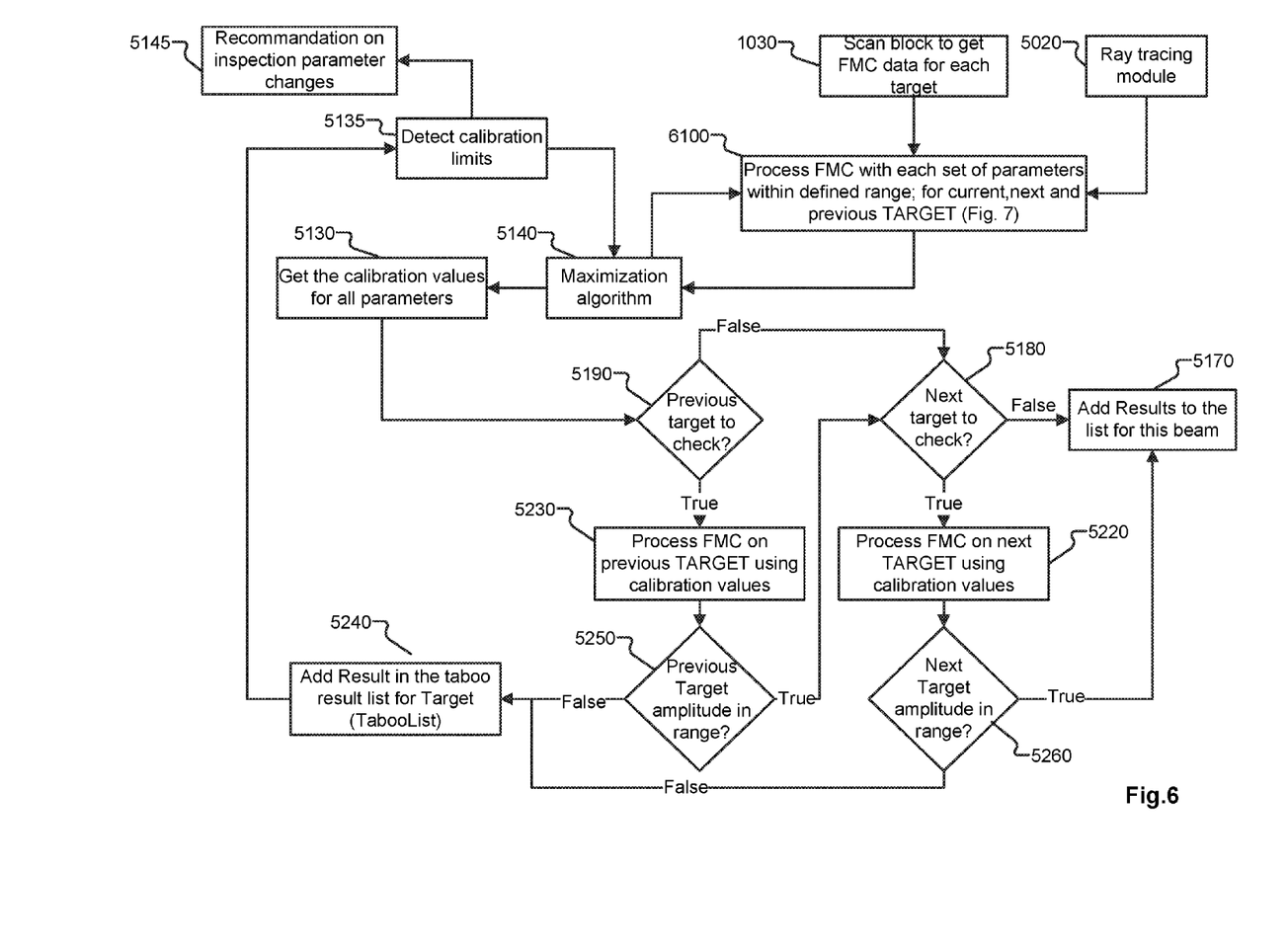
FIG. 6 is a flow chart describing specifically the automated calibration process.

Now looking at the details of 1060 in FIG. 6, we start from the two inputs 1030 and 5020. Inspection results for the current, next and previous TARGET are generated in 6100 by selecting test parameters within the range defined by the ray-tracing and known tolerances for the inspection. Results generated by 6100 are analyzed in 5140 in order to find the configuration that provides a maximal response on the current TARGET. A feedback from 5140 to 6100 makes it possible to orient the parameters search through the use of a Tabu search algorithm (which is part of 5140). Short term Tabu list values (i.e. list of values to avoid) generated during this search expire after step 5140 completion. Tabu search algorithms are well known in the art to perform such task.

Results of step 5140 are the calibration values 5130, which are then used for the previous and next TARGET analysis. A calibration value 5130 includes all relevant acoustic parameter such as transmitter and receiver aperture definition, focalization and steering angle. Step 5180 and 5190 account for the need of this alternate test for the application and the specific TARGET being evaluated. For cases where previous TARGET 221 validation is required, the FMC data corresponding to the acquisition of the previous TARGET 221 at scan position $SP_{221}$ are processed with calibration values 5130 by finding the maximum amplitude recorded $P_{221}$ within the scan position tolerances of $SP_{221}$. Obviously, if the resulting amplitude is within the expected range the process goes on for an equivalent validation on the next target if needed. In cases where the resulting amplitude isn't in the desired range, the current calibration values are put in the long term Tabu list of the Tabu search algorithm.

A further validation is a search for conditions that prevent a solution to be found within the defined tolerance and with the current FMC data set, the extreme case being that all possible combination of parameters have been evaluated without success. This validation is represented by block 5135, a specific condition can lead to a decision that the probe assembly 3000 must be moved in order to find a solution or that tolerance must be increased by monitoring the evolution of the long term Tabu list and the associated trend on the step 5250 and 5260 validation results. Once calibration values are found that satisfies both 5250 and 5260, the calibration of the beam for the current TARGET is completed and the calibration values are saved for further steps.

Figure 7:
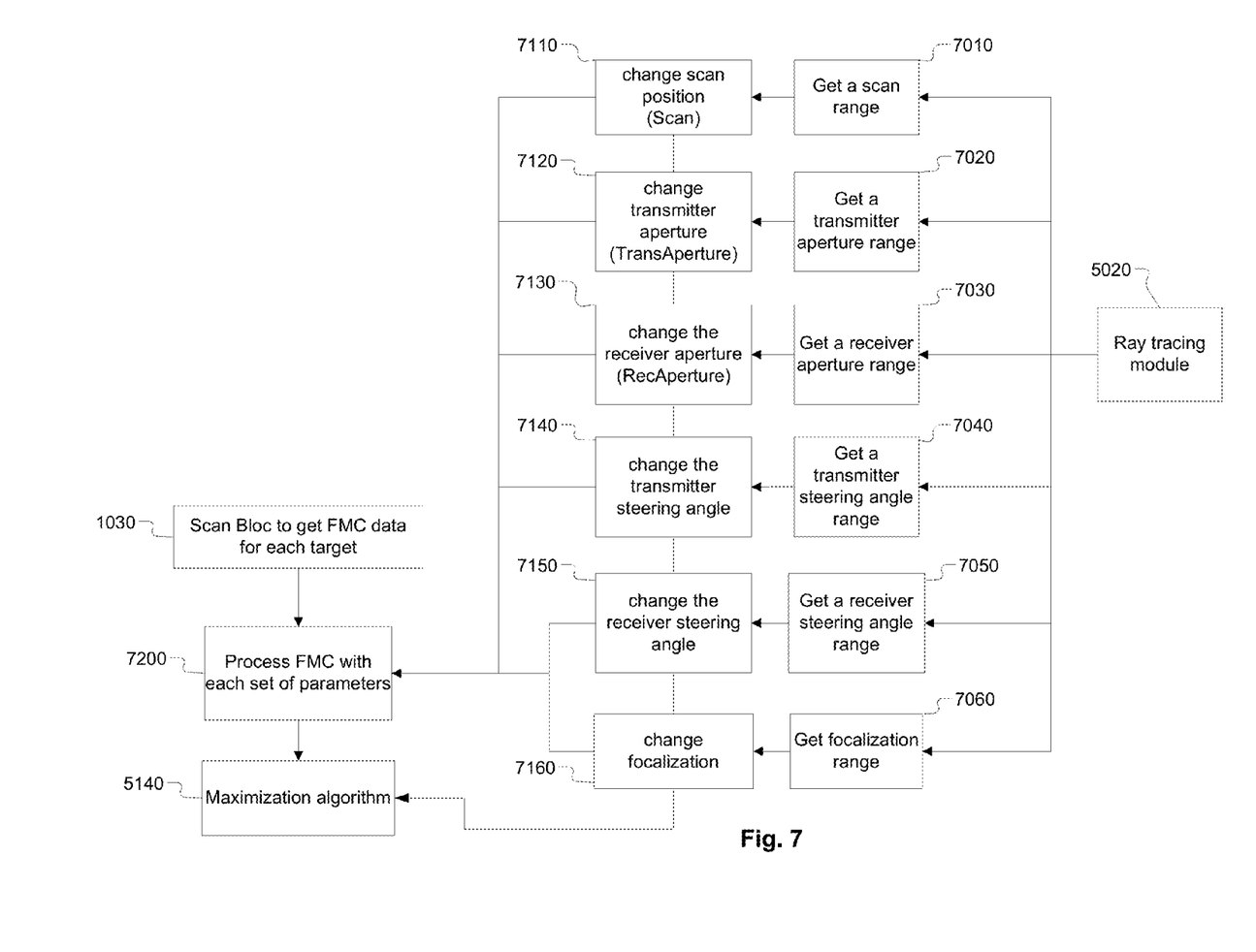
FIG. 7 is a flow chart describing a particular aspect of the automated calibration process which is the iterative generation of test parameter within defined range.

Now looking at FIG. 7, we have a detailed overview of the various sub-steps involved in 6100. Block 7010 represents the allowed scan position range while other blocks 7020, 7030, 7040, 7050 and 7060 represent acceptable range for the various acoustic parameters corresponding to the calibration values themselves. Specific parameters to be used for the processing of FMC data within 7200 are represented by 7110, 7120, 7130, 7140, 7150 and 7160. The specific selection of those parameters is oriented by the maximization algorithm 5140.

It must be understood that although the automated calibration process is described here for PAUT girth weld inspection, it could also be used for other pitch-catch PAUT inspections as long as the calibration process is based on the use of PAUT beams to be set on a calibration block with known acoustic reflectors.

It must also be understood that the calibration values provided as a result of the invention in 1090 can be used either for further inspection with PAUT or/and FMC acquisition.

It should be noted the FMC is often known to deploy phased array operations involving all elements in a matrix probe. However, with the same operational principle used by the conventionally known FMC, the techniques involved in the present disclosure can optionally include those operations that only use a portion of the matrix element. This applies to both transmitting and receiving side of operations, and to the situations when the number of elements on the transmitting side differs from that on the receiving side. The variation depends on how the apertures are selected and arranged, all of which should be understood by those skilled in the art and are all within the scope of the present disclosure.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed:

1. A calibration method for calibrating a phased array inspection system configured for conducting inspection on a test object, the system including a probe having a plurality of apertures, the method comprising the steps of:
defining a series of target zones on a calibration block,
placing the probe via a coupling medium relative to the calibration block;
providing the system with a set of physical parameters pertaining to the system, the coupling medium, the probe and the type of the test object,
employing the system to conduct ray-tracing to provide an initial set of acoustic parameters which define respective aperture position and steering angle for at least a transmitting aperture and a receiving aperture;
employing a full matrix capture (FMC) acquisition process and automatically scanning the block to obtain full or partial FMC data for each of the target zones;
automatically analyzing and optimizing the values of the initial set of acoustic parameters to obtain a final set of acoustic parameters for the system; and,
automatically configuring the system with the final set of acoustic parameters to enable the system to conduct inspection on the test object;
wherein the final set of acoustic parameters includes an aperture width, a steering angle, and a focalization law respectively for a transmitter mode and a receiver mode of the system.

2. The method of claim 1, wherein the test object is a weld line.

3. The method of claim 1, including utilizing the system for detecting planar flaws in a girth weld.

4. The method of claim 1, wherein the initial set of acoustic parameters include a first set of delays for the transmitting aperture and a second set of delays for the returning aperture.

5. The method of claim 1, wherein the calibration block has target reflectors which represent the target zones.

6. The method of claim 1, wherein the full matrix capture data is acquired at each respective scan position for each of the target zones.

7. The method of claim 1, wherein a ray-tracing module provides known information for the system and the coupling medium which includes the size and pitch of the probe elements, as well as the localization of these elements relative to an upper surface of the test object.

8. The method of claim 7, wherein physical parameters of the test object, including the thickness of the test object is provided to a ray-tracing process.

9. The method of claim 1, including utilizing a Tabu search algorithm to find maximal response points during calibration of the system.

10. The method of claim 1, wherein the calibration process is performed automatically.

11. The method of claim 1, wherein the probe uses a pitch-catch mode of operation between the transmitting and receiving apertures.

12. A calibration method for calibrating a phased array inspection system configured for conducting inspection on a test object, the system including a probe having a plurality of apertures, the method comprising the steps of:
defining a series of target zones on a calibration block,
placing the probe via a coupling medium relative to the calibration block;
providing the system with a set of physical parameters pertaining to the system, the coupling medium, the probe and the type of the test object,
employing the system to conduct ray-tracing to provide an initial set of acoustic parameters which define respective aperture position and steering angle for at least a transmitting aperture and a receiving aperture;
employing a full matrix capture (FMC) acquisition process and automatically scanning the block to obtain full or partial FMC data for each of the target zones;
automatically analyzing and optimizing the values of the initial set of acoustic parameters to obtain a final set of acoustic parameters for the system; and,
automatically configuring the system with the final set of acoustic parameters to enable the system to conduct inspection on the test object;
wherein the final set of acoustic parameters is selected such that at each given target zone the system obtains an amplitude reading such that corresponding amplitude readings at target zones that are immediately adjacent to the given target zone are within a predetermined amplitude differential value from that at the given target zone.

13. The method of claim 12, wherein the predetermined amplitude differential value is 10 dB or greater.

14. The method of claim 12, wherein the step of optimization including obtaining an indication output that indicates to a user that the probe placement relative to the calibration block should be altered in order to achieve the final set of acoustic parameters.

15. The method of claim 12, including carrying out a validation process to make a determination wherein the probe must be moved in order to find a solution wherein the predetermined amplitude differential value is achieved for all target zones.

* * * * *